United States Patent
Graves et al.

(10) Patent No.: US 10,761,100 B2
(45) Date of Patent: Sep. 1, 2020

(54) SYSTEMS, ASSAYS, AND METHODS FOR DETERMINING RISK FACTORS FOR ALZHEIMER'S DISEASE

(71) Applicant: Brigham Young University, Provo, UT (US)

(72) Inventors: Steven W. Graves, Provo, UT (US); John S. K. Kauwe, III, Provo, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 15/323,718

(22) PCT Filed: Jul. 1, 2015

(86) PCT No.: PCT/US2015/038914
§ 371 (c)(1),
(2) Date: Jan. 3, 2017

(87) PCT Pub. No.: WO2016/004259
PCT Pub. Date: Jan. 7, 2016

(65) Prior Publication Data
US 2017/0138964 A1    May 18, 2017

Related U.S. Application Data (60) Provisional application No. 62/019,782, filed on Jul. 1, 2014.

(51) Int. Cl.
*A61K 38/00* (2006.01)
*C12Q 1/68* (2018.01)
*G01N 33/567* (2006.01)
*G01N 33/68* (2006.01)

(52) U.S. Cl.
CPC ..... *G01N 33/6896* (2013.01); *G01N 33/6848* (2013.01); *G01N 2800/2821* (2013.01)

(58) Field of Classification Search
None
See application file for complete search history.

(56) References Cited

FOREIGN PATENT DOCUMENTS

| WO | WO 2012/168561 A1 | 12/2012 |
| WO | WO 2013/096862 A2 | 6/2013 |
| WO | WO 2013151726 A1 | 10/2013 |

OTHER PUBLICATIONS

PCT Application No. PCT/US15/38914, Filing Date Jul. 1, 2015, Steven W. Graves, International Search Report, dated Oct. 13, 2015, 7 pages.
Shah, "Discovery of Novel Serum Biomarkers for Diagnosing and Staging Alzheimer's Disease." Brigham Young University; BYU Scholars Archive; Jun. 1, 2014; 196 pages.
Tonminaga et al, "Molecular Probes in Tandem Electrospray Ionization Mass Spectrometry: Application to Tracing Chemical Changes of Specific Phospholipid Molecular Species." American Journal of Analytical Chemistry; Scientific Research; 2013; vol. 4; pp. 16-26.
Kekkonen et al.; "Effect of Probiotic Lactobacillus Rhamnosus GG Intervention on Global Serum Lipidomics Profiles in Healthy Adults," World Journal of Gastroenterology; (May 28, 2008); pp. 3188-3194 vol. 14, No. 20; <doi: 10.3748/WJG.14.3188>.
Koulman et al.; "High-Resolution Extracted Ion Chromatography, a New Tool for Metabolomics and Lipidomics using a Second Generation Orbitrap Mass Spectrometer;" Rapid Communications in Mass Spectrometry; (May 30, 2009); pp. 1411-1418; vol. 23; <doi: 10.1002/rcm.4015>.
Mapstone et al.; "Plasma Phospholipids Identify Antecedent Memory Impairment in Older Adults;" Nature Medicine; (Jan. 1, 2014); pp. 415-418; vol. 20, No. 4; <doi: 10.1038/nm.3466 >.
Pubchem; PC(20:5(5Z,8Z,11Z,14Z,17Z)/18:2(9Z,12Z)); Human Metabalome Database (HMDB); (Jun. 9, 2011); 13 pages.
Partial European Search Report dated May 15, 2020, in EP Application No. 19201752.3, dated Jul. 1, 2015; 5 pages.

*Primary Examiner* — Olga N Chernyshev
(74) *Attorney, Agent, or Firm* — Thorpe North & Western, LLP (57) ABSTRACT

A method of determining risk factors for Alzheimer's disease in an individual, including assaying a biological medium obtained from the individual for a biomarker selected from Biomarker 1, Biomarker 2, Biomarker 3, or Biomarker 4, where Biomarker 1 has a mass-to-charge ratio (m/z) of 602.3, Biomarker 2 has a m/z of 804.6, Biomarker 3 has a m/z of 874.6, and Biomarker 4 has a m/z of 804.5, and where the presence of the two or more biomarkers in the individual indicates a risk factor of Alzheimer's disease.

9 Claims, 2 Drawing Sheets
Specification includes a Sequence Listing.

SYSTEMS, ASSAYS, AND METHODS FOR DETERMINING RISK FACTORS FOR ALZHEIMER'S DISEASE

PRIORITY DATA

This application is a 371 U.S. Nationalization of International Patent Cooperation Treaty (PCT) Application Serial No. PCT/US2015/038914, filed Jul. 1, 2015, which claims the benefit of U.S. Provisional Patent Application Ser. No. 62/019,782, filed on Jul. 1, 2014, each of which is incorporated herein by reference.

BACKGROUND

Alzheimer's disease (AD) is a debilitating disease for which there is no current cure, which worsens as it progresses, eventually leading to death. Currently there are no generally acceptable biomarkers for AD, and the diagnosis of this condition, while improved, is generally subjective. Often such diagnoses are confirmed late in the disease progression, when damage to neural tissue has limited treatment options. The measurement of amyloid β protein (1-42), tau protein, and phosphorylated tau have been proposed as biomarkers measured in the cerebrospinal fluid (CSF) of symptomatic individuals. These, in conjunction with more sensitive imaging techniques involving the CSF introduction of dyes that target these same proteins, are able to identify some fraction of AD patients, but not at its earliest stage. These approaches are, however, invasive, expensive, and unfeasible as screening techniques.

BRIEF DESCRIPTION OF THE DRAWINGS

For a fuller understanding of the nature and advantage of the present invention, reference is being made to the following detailed description of preferred embodiments and in connection with the accompanying drawings, in which.

DETAILED DESCRIPTION

Before the present disclosure is described herein, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Definitions

The following terminology will be used in accordance with the definitions set forth below:

As used herein, the terms "subject" and "individual" can be used interchangeably, and are intended to refer to a human.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly, and vice versa. Further, it is to be understood that the listing of components, species, or the like in a group is done for the sake of convenience and that such groups should be interpreted not only in their entirety, but also as though each individual member of the group has been articulated separately and individually without the other members of the group unless the context dictates otherwise. This is true of groups contained both in the specification and claims of this application. Additionally, no individual member of a group should be construed as a de facto equivalent of any other member of the same group solely based on their presentation in a common group without indications to the contrary.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

Reference throughout this specification to "an example" or "exemplary" means that a particular feature, structure, or characteristic described in connection with the example is included in at least one embodiment of the present invention. Thus, appearances of the phrases "in an example" or the word "exemplary" in various places throughout this specification are not necessarily all referring to the same embodiment.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

THE DISCLOSURE

There is a need for biomarkers and biomarker assays that can identify an individual with risk factors for Alzheimer's disease (AD), particularly those that rely on easily and inexpensively obtained specimens. Such an identification and subsequent diagnosis can greatly improve the treatment of AD by allowing available treatments to begin as soon as possible. Additionally, biomarkers and biomarker assays capable of detecting very early stage AD can allow for drug studies, especially in non-familial, sporadic AD, which represents 99% of cases.

The present disclosure has utilized a novel serum proteomics approach to elucidate serum biomarkers and biomarker combinations that are linked to AD, including those capable of identifying very early stage AD. An initial serum proteomics study (Biomarker Study I, below) was performed to discover novel molecular biomarkers that were quantitatively different between patients with AD and age, gender, and ApoE4 matched controls, and thus could potentially be used in determining risk factors of AD. Additionally, serum was utilized as the biological medium for the discovery of the biomarkers, thus allowing for easy and inexpensive specimen acquisition in assays developed to screen for such biomarkers. It is noted, however, that the present scope is not limited to serum, and such biomarkers can be assayed for using any biological medium.

In Biomarker Study I, described in more detail below, serum from 58 AD cases with any stage AD (CDR 0.5 to 3) and 55 controls were subjected to the serum proteomics method. For this example, the method focused on quantitative differences in lower molecular weight biomolecules of from about 500 to about 8000 Daltons. The study found 38 molecular species demonstrating significant differences (p<0.05) between cases and controls, with an additional 21 species having near significant differences (p>0.05 but <0.10). These were submitted to statistical approaches that considered combinations of candidates in a way that optimized their diagnostic power. Several combinations of a few markers provided sensitivities of more than 80% (true positives) with specificities of at least 80% (true negatives). There were 13 candidate biomarkers that occurred in more than one multi-marker panel and these were consequently considered more likely to be useful biomarkers.

A follow up study (Biomarker Study II) was performed, as is described in more detail below. This study was largely a replication of the initial study: comparable numbers, same serum proteomic approach, but carried out in a blinded fashion, i.e. no laboratory personnel knew case-control status of the subjects considered in the follow up study. As this was not a discovery study, only those molecules found to be candidates in the first study were tracked in the follow up study. Moreover, the data analysis was begun with the subset of 13 candidate biomarkers deemed most promising based on their recurrence in several multi-marker panels using initial study data.

As a general summary, the follow up study analyzed serum from 68 AD cases and 57 age, gender, ApoE4 matched controls. However, in this AD specimen set there were more very early and early stage AD patients. Specimens were analyzed without knowledge of case control status using the same serum proteomic approach used in the initial study and statistics were performed independently. The 13 candidate biomarkers from the initial study were reassessed to evaluate their performance using this second specimen set.

Furthermore, the 13 candidate biomarkers were subjected to chemical characterization. Two were initially found to be lipid dimers, and were excluded as described below. Six were excluded as they did not replicate, and two more had such low abundances or were so conflated with other peaks that it was difficult to reliably perform quantitation in the follow up study. Three candidates had continued usefulness in the follow up study. Upon closer analysis it was discovered that one of these candidates was actually two distinct compounds, both having very similar masses and both still significantly different in the replication study.

These four biomarkers, all together and in various combinations, can be utilized to diagnose AD with a high degree of accuracy regardless of disease stage, including the remarkable ability to identify individuals with the earliest stage of AD from controls. A summary of the four biomarkers is shown in Table 1. (PC=glycerophosphatidylcholine, Oxo-PC=oxidized glycerophosphatidylcholine). Biomarker 1 is a peptide having the sequence L/IAENR (SEQ ID NO: 001), Biomarker 2 is a glycerophosphatidylcholine, and Biomarkers 3 and 4 are oxidized glycerophosphatidylcholines, as is described in more detail in the Biomarker II Study below.

TABLE 1

P-values followed by direction of effect in AD for proteomics markers.

| Biomarker | marker m/z | 0 vs >0 | 0 vs. >0.5 | 0 vs. 2 | 0 vs 0.5 only | Chem Class |
|---|---|---|---|---|---|---|
| 1 | 602.3 | 0.0014 | 0.0584 | 0.0465 | <0.0001 | peptide + 1 |
| 2 | 804.55 (804.6) | <0.0001 | <0.0001 | <0.0001 | <0.0001 | PC |
| 3 | 874.6 | <0.0001 | 0.0006 | 0.0025 | <0.0001 | Oxo-PC |
| 4 | 804.53 (804.5) | <0.0001 | <0.0001 | <0.0001 | <0.0001 | Oxo-PC |

Thus in one example, one or more of biomarkers 1-4 can be utilized in the diagnosis of AD in a subject. In some cases, one or more of the biomarkers can diagnose the presence or absence of AD in the subject. In other cases, the one or more biomarkers can diagnose subjects at a very early stage of AD (e.g. CDR 0.5). In other aspects, one or more biomarkers can be used to diagnose the absence of AD in an individual.

Accordingly, in one example a method for determining whether an individual is at risk for AD, or in other words, determining an individual's risk factors for AD, or identifying a risk factor for AD, can include assaying a biological medium obtained from the individual for one or more biomarkers shown in Table 1 (Biomarker 1, Biomarker 2, Biomarker 3, and Biomarker 4), where Biomarker 1 has a mass-to-charge ratio (m/z) of 602.3, Biomarker 2 has a m/z of 804.6, Biomarker 3 has a m/z of 874.6, and Biomarker 4 has a m/z of 804.5. Thus, the presence of the one or more biomarkers in the individual can be diagnostic of AD, or in other aspects can indicate a risk factor for Alzheimer's disease.

In another example, a method for determining whether an individual is at risk for AD, or in other words, determining an individual's risk factors for AD, can include assaying a biological medium obtained from the individual for two or more biomarkers shown in Table 1 (Biomarker 1, Biomarker 2, Biomarker 3, and Biomarker 4), where Biomarker 1 has a m/z of 602.3, Biomarker 2 has a m/z of 804.6, Biomarker 3 has a m/z of 874.6, and Biomarker 4 has a m/z of 804.5. Thus, the presence of the two or more biomarkers in the individual can be diagnostic of AD, or in other aspects can indicate a risk factor for Alzheimer's disease. In another example, the biological medium is assayed for three or more of Biomarkers 1-4. In yet another example, the biological medium is assayed for each of Biomarkers 1-4. In a further example, the biological medium is assayed for Biomarkers 1 and 2. It is thus to be understood that the present scope includes assaying all combinations of Biomarkers 1-4 as any of a number of biomarker panels, including all pairs of biomarkers, all combinations of 3 biomarkers, and all 4 biomarkers together. Furthermore, a biomarker panel can consist of any number of biomarkers from Biomarker 1-4, all combinations of biomarker pairs, all combinations of 3 biomarkers, and all 4 biomarkers together. Such biomarker panels represent novel collections of biomarkers that can be used to detect AD in a subject.

It is additionally noted that, while m/z values are used in the present example to describe each biomarker, any distinguishing characteristic of a biomarker can be utilized, either in addition to or as an alternative for the m/z values. Furthermore, the description of each biomarker by m/z value is for convenience, and should not be construed as an indication that an assay need necessarily utilize MS. Rather, any type of diagnostic technique, device, system, etc., capable of identifying any of the biomarkers in a biological medium is considered to be within the present scope.

That being said, in some examples MS can be useful as an assay or as a component to an assay for determining the presence of any of the biomarkers in the biological medium. In some cases, therefore, the method can further include assaying the biological medium using MS for at least one of the biomarkers. It is noted that a variety of MS techniques and MS systems and system configurations can be utilized, all of which are within the present scope. As one example, tandem MS (MS/MS) can be utilized. In another example, Selected Reaction Monitoring (SRM) can be useful. In another example, Multiple Reaction Monitoring (MRM) can be employed. In another yet another example, chromatographic separation by any of several separation methods coupled to a MS system or used in conjunction with a MS can be considered, e.g. nano-liquid chromatography coupled to a MS instrument or two dimensional liquid chromatography coupled to MS.

Other types of assays can additionally be used, either in conjunction with or as a replacement to a MS procedure. The other type of assay can be used as a confirmation of a biomarker identified by MS, or as a stand-alone assay in the identification of one or more biomarker. In one aspect, for example, any assay that can be utilized to detect a peptide sequence can be used to detect Biomarker 1, either alone or in conjunction with the MS. Various peptide assays are well known in the art, and those of ordinary skill are well versed in their use. One non-limiting example of such an assay can include an antibody assay, such as an ELISA. Furthermore, any assay capable of detecting a glycerophosphatidylcholine or an oxidized glycerophosphatidylcholine is considered to be within the present scope, and can be used to detect any of Biomarkers 2-4. As with peptides, one possibility is the use of an antibody assay designed to detect a glycerophosphatidylcholine, or an oxidized group of a glycerophosphatidylcholine.

Regarding the biological material being assayed, the biological medium can be any biological component of the subject that can include any of the biomarkers of interest. Such can include any tissue, liquefied tissue, bodily fluid, excretion, secretion, and the like. In one example, the biological medium can be a biological fluid. Examples can include whole blood, serum, plasma, urine, lymph, cerebrospinal fluid (CSF), and the like. In one specific example the biological fluid can be serum.

Biomarker Study 1

The following study is one example of obtaining a number of potential AD biomarkers and generating potentially useful multi-marker panels from subject samples. It should be understood that this is merely one approach, and that the methodologies, techniques, and results should not be seen as limiting to the overall scope of the disclosure. That being said, the following study provided data to suggest that at least 82 different observed mass spectrometer peaks might contribute to the diagnosis of AD. These 82 markers were used to investigate multi-marker panels, some of which are described herein. In one example, 13 markers occurred in at least 10% of the panels. Additional investigation of these 13 markers is as follows.

Sample Collection and Study Population

Serum specimens were obtained from the Knight Alzheimer's Disease Research Center (ADRC) at the Washington University School of Medicine, St. Louis, Mo. (WUSTL). Previously collected serum specimens from cases (n=58) and controls (n=55) were provided. The cases represented AD patients with different clinical dementia ratings (CDR), particularly: mild cognitive impairment (CDR=0.5, n=7) or very early stage AD, early stage AD (CDR=1, n=4), moderate AD (CDR=2 n=19) and severe AD, (CDR=3 n=28). The 58 cases and 55 controls did not have co-morbidities, including diabetes. Specimens were collected and processed into serum according to a uniform method and were stored at −80° C. as serum prior to shipment to Brigham Young University (BYU), before processing at BYU, and after processing at BYU. Specimens were transferred on dry ice.

Sample Processing

Serum contains many highly abundant proteins like albumin. Highly abundant proteins lead to ion suppression of low abundance biomolecules when analyzed by mass spectrometry (MS). This prevents hundreds or thousands of molecular species from appearing in the MS. Hence, in the novel approach used here, these larger proteins are removed using an acetonitrile precipitation protocol. This substantially increases the number of biomolecules observable by MS. It also displaces many small molecules, particularly peptides, from large carrier proteins.

Sera to be studied were thawed on ice, and aliquots of 200 µL were removed for use. To this, 400 µL of HPLC grade acetonitrile was added immediately, vortexed for 20 sec, and allowed to sit at room temperature for 30 min to accomplish protein depletion. Post centrifugation (10000 rpm), the supernatant (~550 µL) was transferred to a clean tube and 300 µL of HPLC grade water was added. The samples were then evaporated to ~200 µL (the original volume of the aliquot) in a vacuum centrifuge (Labconco CentriVap Concentrator, Labconco Corporation, Kansas City, Mo.). This step helps remove the final traces of acetonitrile.

Apparent protein concentration was determined by Bio-Rad microplate protein assay performed according to manufacturer's instructions (Bio-Rad Laboratories, Hercules, Calif.). An aliquot containing an apparent protein concentration of 2 µg was transferred to a new microcentrifuge tube and brought down to <10 µL in a vacuum centrifuge. Samples were brought up to 10 µL with HPLC water and acidified with addition of 10 µL 88% formic acid.

Analysis of Sera on a Capillary-LC-ESI-QTOF Mass Spectrometry System

The protein-depleted, acidified sample was loaded onto a capillary liquid chromatography (cLC) system capable of gradient elution to separate compounds according to their polarities. The column is interfaced with a tandem mass spectrometer. Samples were randomized to keep bias to a minimum and sample sets were run in as short a time as possible to maintain reproducibility. The pump used was an LC Packings Ultimate Capillary HPLC pump system, with a FAMOS autosampler (Dionex Corporation, Sunnyvale, Calif.) maintained at 4° C. The quaternary pump delivers two different solutions: an aqueous solution (98% HPLC grade $H_2O$, 2% acetonitrile and 0.1% formic acid) and an organic solution (2% $H_2O$, 98% acetonitrile and 0.1% formic acid) at a specified composition via a mixing device situated prior to the pump. A 1 mm (16.2 µL) microbore guard column from Upchurch Scientific, Oak Harbor, Wash. and a 15 cm×250 µm i.d. capillary analytical column made in-house were utilized for bringing about chromatographic separation. While the capillary column was slurry packed, the guard column was dry-packed. Both columns used POROS R1 reversed-phase media from Applied Biosystems, Framingham, Mass. The protein-depleted sample was introduced and retained on the guard column and then placed in series with the analytical capillary column and fractionated using the following gradient: 3 min of 95% aqueous and 5% organic phase, followed by a linear rise in organic phase to 60% over the next 24 min. Thereafter, the solvent mix was increased linearly to 95% organic phase and 5% aqueous phase over the next 7 min, then held at 95% organic phase for 7 min, and returned to 95% aqueous phase over 5 min. The column was allowed to re-equilibrate until the end time of the run (58 min). The flow rate used was 5.0 µL/min.

The cLC system was interfaced via an IonSpray source from Applied Biosystems to a QSTAR Pulsar I quadrupole/orthogonal time-of-flight mass spectrometer set at 4800V. MS data was collected for m/z range of 500 to 2500 starting at 5 min and ending at 55 min of gradient elution. The positive ion mode was used with the scan rate of 1 spectrum/sec. The software package of Analyst QS® permitted effective data collection, preliminary formatting, MS spectral comparison, extraction of specific ion chromatograms and analysis.

Time Normalization of the MS Data

Given some variability in chromatographic elution times from one sample to another, a series of 10 endogenous molecular species, consistently present in all specimens, were selected as internal elution time standards. The species of the series elute at approximately two minutes intervals one from another. These species then allow for the same time window to be considered for each specimen run. Data are organized in two-minute windows centroided on each marker, or where there were gaps between two time markers. The time markers allowed for time normalization, providing uniformity in chromatographic elution windows over the important chromatographic region (~15 to ~35 min).

Selecting Candidate Biomarkers

MS spectra taken from 1 min before to 1 min after each endogenous time marker were compiled for each sample to generate a composite spectrum. In turn, spectra from AD cases and normal controls were color coded and overlaid to allow for direct visual analysis of each individual molecular species. Peaks that appeared quantitatively different between cases and controls were then further evaluated. This involved the determination of peak height by extracting the ion counts of the desired peak specifying an m/z range to capture the peak envelope maximum using the "XIC" function of the MS instrument software for each of the samples. The peak heights were then recorded for all the samples for each of the potential AD biomarkers and the data tested for statistical significance by Student's t-test. A p-value <0.05 was considered statistically different.

Normalization of the Candidate Biomarkers

Non-biological variability is part of proteomic studies. Sources include variability in specimen processing, specimen stability, ionization efficiency, and instrument sensitivity, among other things. To reduce variability, a previously tested approach was used. A set of native serum molecules was selected as internal references. The ideal reference was present in the same time window, had similar m/z, was consistently there, well separated from other peaks, was easily measured and quantitatively comparable between cases and controls. Each of these was then used to normalize a potential biomarker to compensate for the non-biologic variability between samples. The peak intensity of a candidate biomarker species was ratioed to the intensity of a co-eluting species. Normalization with the use of such an endogenous control typically improved the statistical difference between cases and controls for candidate peaks. Unnormalized raw and log normalized values were calculated for each of the potential biomarker candidates and retested statistically. Again, a p-value <0.05 was used to define candidate serum biomarkers.

Bio-Statistical Analysis

In addition to the Student's t-test that was applied to the initial data screen, other statistical tests were carried out. Logistic regression analysis was used to generate receiver operator characteristic curves for each of the candidate biomarkers to find their sensitivities and specificities. Sensitivity is defined as the fraction of cases correctly identified by a given biomarker. In other words, the cases represent the AD diagnosis given to the subjects that provided the samples, and such diagnosis was made by clinicians and researchers at the Knight ADRC. Specificity reflects the fraction of controls correctly defined by a given biomarker, or in other words, the fraction of controls that were true negative controls correctly identified by the biomarker. Then two or more candidate markers were modeled to obtain combinations that provided better diagnostic discrimination. All biomarker candidates with p-values less than 0.10 were considered because there is likelihood that some of these may be complementary to other candidate biomarkers even if they themselves do not satisfy criteria for statistical significance. Logistic regression analysis was also used to evaluate combinations of biomarkers to model the log-odds of developing AD. Finally, a forward-selection statistical procedure was used. In this approach, the candidate markers were added to the model one at a time, beginning with each individual marker. The inclusion of other markers on a one by one basis was tested to see if the combination of the markers increased the area under the receiver operator curve (AUC, a measure of overall diagnostic utility) of at least 0.03. In this way it was possible to obtain combinations of biomarkers giving the highest possible AUCs. This defines our 'leave-one out' prediction approach. Several potentially useful panels of AD biomarkers were obtained this way. ROC curves were plotted once again to study the combined sensitivities and specificities of these multi-marker models.

Results—Biomarker Study 1

Candidate Serum AD Diagnostic Biomarkers

When studying raw, un-normalized mass spectral data, we found 44 candidate serum AD biomarkers that were statistically significant in the all-stage AD set (CDR=0.5, 1, 2, 3) compared with the matched, non-demented controls set (CDR=0). There were additionally 25 biomarkers that had p-values between 0.05 and 0.10. With log normalizing the data for each candidate to an endogenous molecular reference species (that was equivalently distributed between cases and controls), there remained 38 significantly different serum biomarkers and 21 candidates that were near significant (p=0.05 to <0.10). Many of these were significantly different in both raw and normalized data sets. A summary of all 82 of these potential AD biomarkers is provided in Table 2. In addition each candidate was submitted to receiver operator characteristic curve analysis. While some of the AD biomarkers were increased or up-regulated in quantity, others were decreased in subjects with AD.

TABLE 2

Biomarkers considered for biostatistical analysis in the initial study having significant (<0.05) or near significant (<0.1) p-values.

| Candidate number | Elution time window (min) | m/z of biomarker | Charge (Positive ion mode) | p value for ratio of pot. biomarker to ref. biomarker | p value for log of ratio of pot. biomarker to ref. biomarker | p value for unnormalized pot. biomarker | p value for unnormalized ref. biomarker |
|---|---|---|---|---|---|---|---|
| 1 | 8-15 | 921.4 | 1 | 0.0494 | 0.035 | 0.0214 | 0.4524 |
| 2 | 8-15 | 1091.4 | 1 | 0.0857 | 0.0192 | 0.0538 | 0.4472 |
| 3 | 8-15 | 752.3 | 2 | 0.1565 | 0.1189 | 0.0878 | 0.3806 |
| 4 | 11-15 | 531.3 | 1 | 0.0449 | 0.0414 | 0.0635 | 0.487 |
| 5 | 11-15 | 515.3 | 1 | 0.1249 | 0.0482 | 0.0052 | 0.487 |
| 6 | 11-15 | 1107.5 | 1 | 0.0731 | 0.0218 | 0.1535 | 0.487 |
| 7 | 11-15 | 561.2 | 1 | 0.0866 | 0.1615 | 0.2144 | 0.487 |
| 8 | 11-15 | 574.3 | 1 | 0.0778 | 0.3269 | 0.3238 | 0.487 |
| 9 | 11-15 | 597.8 | 2 | 0.386 | 0.3673 | 0.0703 | 0.487 |
| 10 | 11-15 | 602.3 | 1 | 0.0905 | 0.0787 | 0.1492 | 0.487 |
| 11 | 11-15 | 690.8 | 2 | 0.072 | 0.3121 | 0.3938 | 0.487 |
| 12 | 11-15 | 701.8 | 2 | 0.0865 | 0.0946 | 0.0684 | 0.487 |
| 13 | 11-15 | 708.3 | 1 | 0.0812 | 0.2063 | 0.0762 | 0.487 |
| 14 | 11-15 | 821.3 | 1 | 0.0606 | 0.045 | 0.1389 | 0.487 |
| 15 | 11-15 | 892.4 | 1 | 0.1487 | 0.217 | 0.0392 | 0.487 |
| 16 | 11-15 | 971.4 | 1 | 0.0836 | 0.0986 | 0.2517 | 0.487 |
| 17 | 11-15 | 1194.5 | 1 | 0.1015 | 0.0854 | 0.1503 | 0.487 |
| 18 | 11-17 | 1396.6 | 1 | 0.0506 | 0.0919 | 0.1442 | 0.2468 |
| 19 | 13-19 | 587.3 | 1 | 0.0918 | 0.014 | 0.0785 | 0.2468 |
| 20 | 13-19 | 989.3 | 4 | 0.0952 | 0.1129 | 0.094 | 0.4886 |
| 21 | 13-19 | 791.6 | 5 | 0.1144 | 0.1405 | 0.0837 | 0.4886 |
| 22 | 16-22 | 748.6 | 1 | 0.1808 | 0.1143 | 0.0309 | 0.3663 |
| 23 | 16-22 | 704.5 | 1 | 0.0831 | 0.04 | 0.0149 | 0.3663 |
| 24 | 16-22 | 778.6 | 1 | 0.0416 | 0.0214 | 0.0136 | 0.3663 |
| 25 | 16-22 | 583.3 | 1 | 0.0115 | 0.0379 | 0.0002 | 0.3663 |
| 26 | 16-22 | 660.5 | 1 | 0.1229 | 0.0533 | 0.0258 | 0.3663 |
| 27 | 16-22 | 734.5 | 1 | 0.0678 | 0.0278 | 0.0157 | 0.3663 |
| 28 | 16-22 | 924.6 | 1 | 0.2164 | 0.1387 | 0.0822 | 0.3663 |
| 29 | 16-22 | 880.6 | 1 | 0.1696 | 0.0729 | 0.0569 | 0.3663 |
| 30 | 16-22 | 822.5 | 1 | 0.1146 | 0.0584 | 0.0312 | 0.3663 |
| 31 | 16-22 | 819.5 | 1 | 0.1701 | 0.2171 | 0.0813 | 0.3663 |
| 32 | 16-22 | 616.4 | 1 | 0.1363 | 0.0652 | 0.0177 | 0.3663 |
| 33 | 16-22 | 626.4 | 1 | 0.0534 | 0.1264 | 0.0703 | 0.3663 |
| 34 | 17-25 | 502.3 | 1 | 0.1083 | 0.1636 | 0.0028 | 0.147 |
| 35 | 17-25 | 512.4 | 1 | 0.2105 | 0.1737 | 0.0297 | 0.147 |
| 36 | 17-25 | 518.3 | 1 | 0.2331 | 0.2397 | 0.0516 | 0.147 |
| 37 | 17-25 | 520.3 | 1 | 0.375 | 0.4531 | 0.029 | 0.3837 |
| 38 | 17-25 | 542.4 | 1 | 0.1347 | 0.0975 | 0.0051 | 0.147 |
| 39 | 17-25 | 560.4 | 1 | 0.0263 | 0.0219 | 0.055 | 0.147 |
| 40 | 17-25 | 564.3 | 1 | 0.0845 | 0.0226 | 0.001 | 0.147 |
| 41 | 17-25 | 614.4 | 1 | 0.1679 | 0.0674 | 0.1048 | 0.147 |
| 42 | 17-25 | 629.4 | 1 | 0.2842 | 0.1131 | 0.0428 | 0.3837 |
| 43 | 17-25 | 687.4 | 2 | 0.148 | 0.0203 | 0.0614 | 0.147 |
| 44 | 17-25 | 701.5 | 1 | 0.2589 | 0.0862 | 0.0211 | 0.3837 |

TABLE 2-continued

Biomarkers considered for biostatistical analysis in the initial study having significant (<0.05) or near significant (<0.1) p-values.

| Candidate number | Elution time window (min) | m/z of biomarker | Charge (Positive ion mode) | p value for ratio of pot. biomarker to ref. biomarker | p value for log of ratio of pot. biomarker to ref. biomarker | p value for unnormalized pot. biomarker | p value for unnormalized ref. biomarker |
|---|---|---|---|---|---|---|---|
| 45 | 17-25 | 804.6 | 1 | 0.055 | 0.0188 | 0.0555 | 0.1461 |
| 46 | 17-25 | 861.6 | 1 | 0.3184 | 0.1943 | 0.043 | 0.3837 |
| 47 | 17-25 | 938.7 | 1 | 0.0838 | 0.0464 | 0.0385 | 0.147 |
| 48 | 17-25 | 1021.7 | 1 | 0.3016 | 0.4593 | 0.0808 | 0.147 |
| 49 | 17-25 | 1126.8 | 1 | 0.0313 | 0.0148 | 0.0215 | 0.147 |
| 50 | 17-25 | 1156.9 | 1 | 0.108 | 0.0663 | 0.1175 | 0.147 |
| 51 | 17-25 | 1170.9 | 1 | 0.044 | 0.0212 | 0.0332 | 0.147 |
| 52 | 20-27 | 544.3 | 1 | 0.3909 | 0.3928 | 0.0085 | 0.4623 |
| 53 | 22-32 | 513.3 | 1 | 0.0079 | 0.0163 | 0.0228 | 0.1225 |
| 54 | 22-32 | 660.4 | 1 | 0.0186 | 0.0113 | 0.0579 | 0.0984 |
| 55 | 22-32 | 568.4 | 1 | 0.4693 | 0.4398 | 0.0347 | 0.1243 |
| 56 | 25-34 | 530.4 | 1 | 0.0201 | 0.0183 | 0.2205 | 0.4059 |
| 57 | 25-34 | 790.6 | 1 | 0.0636 | 0.0506 | 0.0872 | 0.4059 |
| 58 | 25-34 | 830.6 | 1 | 0.0558 | 0.013 | 0.047 | 0.4059 |
| 59 | 25-34 | 848.6 | 1 | 0.03 | 0.0048 | 0.014 | 0.4059 |
| 60 | 25-34 | 856.6 | 1 | 0.0155 | 0.0034 | 0.0162 | 0.4059 |
| 61 | 25-34 | 878.6 | 1 | 0.0424 | 0.0085 | 0.0243 | 0.4059 |
| 62 | 25-34 | 535.4 | 1 | 0.0869 | 0.1409 | 0.2034 | 0.4059 |
| 63 | 25-34 | 653.4 | 1 | 0.0973 | 0.1098 | 0.1767 | 0.4059 |
| 64 | 25-34 | 804.6 | 1 | 0.1639 | 0.0822 | 0.1522 | 0.4059 |
| 65 | 29-37 | 1540.2 | 1 | 0.0278 | 0.027 | 0.002 | 0.4417 |
| 66 | 29-37 | 744.6 | 1 | 0.2436 | 0.2068 | 0.0332 | 0.448 |
| 67 | 29-37 | 730.6 | 1 | 0.1185 | 0.0971 | 0.087 | 0.448 |
| 68 | 29-37 | 874.6 | 1 | 0.1235 | 0.0044 | 0.0133 | 0.448 |
| 69 | 29-37 | 758.6 | 1 | 0.2079 | 0.2869 | 0.0152 | 0.448 |
| 70 | 29-37 | 1516.2 | 1 | 0.017 | 0.016 | 0.0223 | 0.448 |
| 71 | 31-38 | 808.6 | 1 | 0.0075 | 0.0057 | 0.0002 | 0.1961 |
| 72 | 31-38 | 675.6 | 1 | 0.1845 | 0.0713 | 0.0912 | 0.1961 |
| 73 | 31-38 | 784.6 | 1 | 0.0466 | 0.0409 | 0.0886 | 0.1961 |
| 74 | 31-38 | 1618.2 | 1 | 0.0086 | 0.0119 | 0.0161 | 0.1961 |
| 75 | 31-38 | 1592.2 | 1 | 0.0093 | 0.01 | 0.014 | 0.1961 |
| 76 | 31-38 | 810.6 | 1 | 0.0044 | 0.0049 | 0.0022 | 0.1961 |
| 77 | 31-38 | 834.6 | 1 | 0.0384 | 0.0402 | 0.0616 | 0.1961 |
| 78 | 31-38 | 1568.2 | 1 | 0.0018 | 0.002 | 0.0014 | 0.1961 |
| 79 | 31-38 | 1576.2 | 1 | 0.0214 | 0.0089 | 0.0179 | 0.1961 |
| 80 | 31-38 | 1642.2 | 1 | 0.0609 | 0.0608 | 0.1092 | 0.1961 |
| 81 | 31-38 | 1616.2 | 1 | 0.0754 | 0.0655 | 0.194 | 0.1961 |
| 82 | 31-38 | 832.6 | 1 | 0.4754 | 0.4653 | 0.0068 | 0.1961 |

Evaluation of the Biomarkers in Multi-Marker Panels

Differences in staging, gender, the type of pathology present, and potentially even its cause may, in some cases, lead to different biochemical changes in different patients. Use of a single biomarker may thus fail in some cases to identify all individuals with a given condition. Because of this, there is often improved diagnostic ability achieved with appropriate multi-marker sets. Hence, we tested combinations of our serum biomarkers to see if they would provide improved diagnostic discrimination for AD. As described above, a forward selection approach was used to construct multiple marker panels. This considered all of the candidates, recognizing that even biomarkers that were only near significant might add complementary diagnostic information on patients with AD. Multi-biomarker panels were created by including statistically different or near different normalized candidates one by one until a combination of the panel yielded the best AUC possible. As mentioned earlier, each model was considered final when no additional marker improved the AUC by more than 0.03. With the construction of these several models, one for each biomarker as the starting point, it was also possible to determine which of those candidate markers showed up in more than one model. Markers occurring in several panels were considered to be the more promising biomarkers and these were considered further. There were 13 biomarkers that appeared in 10% or more of all the multi-marker models (See Table 3).

TABLE 3

A Set of 13 biomarkers that appeared in 10% or more of all the multi-marker models.

| | Elution time window (min) | m/z of biomarker | Charge (Positive ion mode) | p value for ratio of pot. biomarker to ref. biomarker | p value for log of ratio of pot. biomarker to ref. biomarker | p value for unnormalized pot. biomarker | p value for unnormalized ref. biomarker |
|---|---|---|---|---|---|---|---|
| 1 | 11-15 | 531.3 | 1 | 0.0449 | 0.0414 | 0.0635 | 0.4870 |
| 2 | 11-15 | 602.3 | 1 | 0.0905 | 0.0787 | 0.1492 | 0.4870 |
| 3 | 11-15 | 701.8 | 2 | 0.0865 | 0.0946 | 0.0684 | 0.4870 |
| 4 | 11-15 | 708.3 | 1 | 0.0812 | 0.2063 | 0.0762 | 0.4870 |
| 5 | 11-15 | 892.4 | 1 | 0.1487 | 0.2170 | 0.0392 | 0.4870 |
| 6 | 13-19 | 989.3 | 4 | 0.0952 | 0.1129 | 0.0940 | 0.4886 |
| 7 | 16-22 | 583.3 | 1 | 0.0115 | 0.0379 | 0.0002 | 0.3663 |
| 8 | 17-25 | 804.6 | 1 | 0.0550 | 0.0188 | 0.0555 | 0.1461 |
| 9 | 22-32 | 660.4 | 1 | 0.0186 | 0.0113 | 0.0579 | 0.0984 |
| 10 | 29-37 | 874.6 | 1 | 0.1235 | 0.0044 | 0.0133 | 0.4480 |
| 11 | 31-38 | 1618.2 | 1 | 0.0086 | 0.0119 | 0.0161 | 0.1961 |
| 12 | 31-38 | 810.6 | 1 | 0.0044 | 0.0049 | 0.0022 | 0.1961 |
| 13 | 31-38 | 1568.2 | 1 | 0.0018 | 0.0020 | 0.0014 | 0.1961 |

Further statistical studies were carried out on just these 13 biomarkers as a subset. Once again, the forward selection process was performed with complementary correlation analysis, which included dendritic analysis and heat maps. ROC curves were plotted to study the performance of panels of these biomarkers in identifying AD. The best combinations of the 13 biomarkers provided AUCs of 0.908 and 0.912, as is shown in FIGS. 1A-B and 2A-B. The best combinations provided sensitivities of 88% and a specificity of 87%. There were 6 multi-marker models that had an AUC of more than 0.80, where 11 of the 13 best biomarkers repeated themselves.

Biomarker Study 2

The following study replicated portions of the Biomarker Study 1: comparable numbers of subjects included, the same or very similar serum proteomic approach, but was carried out in a blinded fashion, i.e. no individual involved with the laboratory study knew case-control status of the subjects considered in the present study. As such, this was not intended to be a discovery study, so only those molecules found to be candidates in the first study were analyzed in the current MS data. Moreover, the data analysis was initiated with the subset of 13 candidate biomarkers deemed most promising based on their recurrence in several multi-marker panels using initial study data.

In this study, serum was analyzed from 68 AD cases and 57 age, gender, ApoE4 matched controls. However, in this AD specimen set there were many more early stage AD patients. Specimens were analyzed without knowledge of case control status using the same or very similar serum proteomic approach used in the Biomarker Study 1, and statistics were performed independently by an arbiter. However, for this study the instrumental analysis was carried out on a new tandem mass spectrometer that operated identically to the tandem MS used in the initial study, but the new instrument performs more consistently and is more sensitive.

As indicated, the 13 candidate biomarkers that appeared in multiple panels in the first study were initially analyzed. After beginning chemical characterization of the 13 candidate biomarkers, two were found to be lipid dimers. While it is possible that dimerization may happen in the body, studies suggest that it can occur outside the body, perhaps even as part of instrumental analysis. Because of this, these two were considered potentially unreliable and have not been considered further at this time. It is noted, however, that these lipid dimers may be reevaluated in the future and determined to be useful multi-marker panel components, and as such continue to be considered to be within the present scope. Two compounds had such low abundances or were so conflated with other peaks that we could not reliably perform quantitation in the follow up study. Further analysis might be possible, and as such these may be reevaluated and reconsidered in the future. Six other candidate biomarkers were excluded for various reasons.

Three candidates were selected for continued study. Upon closer analysis it was discovered that one of these candidates was actually two distinct compounds, both having very similar masses and both still significantly different in the replication study. These four biomarkers showed excellent utility in the diagnosis of AD regardless of disease stage. Additionally, surprisingly these four biomarkers identified individuals with the earliest stage of AD from controls.

It is additionally noted that while the four biomarkers studied further represent one possible collection of markers in a multi-marker panel, other combinations of markers are additionally contemplated and are considered to be within the present scope.

Samples

A set of 125 serum specimens was obtained from the Knight Alzheimer's Disease Research Center (ADRC) at the Washington University School of Medicine, St. Louis, Mo. (WUSTL). These samples comprised 68 cases having different stages of AD and 57 controls that were non-demented and matched for age, gender and ApoE 4 prevalence. Among the 68 cases, there were 24 samples with CDR=0.5, the lowest stage of AD. This made it possible to test the performance of the biomarkers between non-demented controls (CDR=0) and individuals with mild cognitive impairment (CDR=0.5). The comparison was precluded in Biomarker Study I due to very small number of samples with CDR=0.5 in that set. An independent arbiter, aware of case/control status, created analysis sets that included both cases and controls randomized and submitted to our laboratory for analysis in a blinded fashion. 11 sets of samples, each including 10-13 sera, were analyzed. The sets had approximately the same number of cases and controls, as well as the same number of men and women, to avoid bias due to sample processing, day-to-day changes in instrumental sensitivities, loading and ionization inefficiencies, and the like. All MS data were provided to the arbiter for statistical analysis independent of the laboratory investigators having any knowledge of case/control status.

Validation of Biomarkers

Only one analysis set was processed at a time. Samples were shipped on dry ice and stored at −80° C., pre and post processing. Samples were processed using the acetonitrile precipitation method described in the Biomarker Study I above. Specimens were processed, subsequently loaded, and run on the Agilent 6530 Accurate-Mass Q-TOF LC/MS mass spectrometer system in a single day. All the sets were analyzed in as short a time as possible to minimize chromatographic and instrumental variation. A 45-minute wash run was included between each sample to minimize any carry over from previous samples, while a more significant wash run of 105 min was added at the end of every day. Care was taken to maintain consistency in sample processing, quantitative loading, chromatographic elution profile, and instrument calibration/sensitivity performance across all specimens and all days.

An Agilent 1260 Infinity Series HPLC system equipped with quaternary pump, online degasser, auto sampler, and thermostated column compartment (Agilent Technologies, Karlsruhe, Germany) was used to perform these validation experiments. Injection volumes of 5 µL, containing an apparent protein concentration of 5 µg, were injected onto a 1 mm (16.2 µL) microbore guard column from Upchurch Scientific, Oak Harbor, Wash., in order to retain the specimen and eliminate salts and highly polar compounds. The guard column was then placed in series and sample loaded onto and fractionated by the analytical column (15 cm×250 µm i.d. POROS R1 reversed-phase capillary column, media obtained from Applied Biosystems, Framingham, Mass. and columns were packed in house) with a mobile phase flow rate of 5 µL/min. Mobile phase A was an aqueous solution water/acetonitrile/formic acid (98/2/0.1, v/v/v) and mobile phase B was an organic solution acetonitrile/water/formic acid (98/2/0.1, v/v/v) respectively. The gradient elution began at 100% A for 2 min followed by a 1 min transition from 100% A to 95% A. This in turn was succeeded by a linear increase in organic phase (B) to 60% over the next 24 min. Thereafter, the mobile phase mix was increased linearly to 95% organic phase B/5% aqueous phase A over the next 7 min, then held at 95% organic phase B for 7 min and returned to 95% aqueous phase A over 5 min. The column was allowed to re-equilibrate until the end of the 58 min run.

The cLC was interfaced with an Agilent 6530 Accurate-Mass Quadrupole Time-of-Flight mass spectrometer (QToF MS) equipped by means of an Agilent Dual ESI source. The Dual ESI source was operated in positive ion mode, and instrument parameters were set as follows: sheath gas temperature, 300° C.; sheath gas flow, 5 L/min; nebulizer, 15 psi; dry gas temperature, 300° C.; dry gas flow, 5 L/min; and capillary entrance voltage (VCap), 3500 V. Fragmentor and Skimmer1 were operated at 175 V and 65 V, respectively. The auto sampler temperature was maintained at 4° C. The MS scan data were collected at a rate of 8 spectra/s over the range of m/z 400-3200. Data was acquired in profile mode. The instrument software MassHunter Data Acquisition B.05.01 (Agilent) and MassHunter Qualitative Analysis B.06.00 (Agilent) permitted effective data collection, extracting specific ion chromatograms and post hoc analysis.

Fragmentation and Chemical Identification Studies

Fragmentation, and chemical identification of biomarkers was accomplished by an MS/MS approach using a QSTAR Pulsar I Quadrupole Orthogonal Time-of-Flight Mass Spectrometer and an Agilent 6530 Accurate-Mass Q-TOF LC/MS. Primarily peptides were sequenced using a QSTAR Pulsar I Quadrupole Orthogonal Time-of-Flight Mass Spectrometer while lipid identifications were performed using both instruments.

Peptide Fragmentation Experiments Employing Applied Biosystem's QSTAR Pulsar I Quadrupole Orthogonal Time-of-Flight Mass Spectrometer The cLC system was interfaced to a QSTAR Pulsar I quadrupole orthogonal time-of-flight mass spectrometer through an ESI IonSpray source (Applied Biosystems) set at 4800V. All experiments were carried out in positive ion mode. Samples run earlier were examined to find samples that naturally had a high concentration of the biomarker of interest. Samples were processed using acetonitrile precipitation and loaded as described above. Prior to MS2 runs, MS1 runs were undertaken to determine the elution time. For MS2 runs, 2-3 times the original amount of protein-depleted serum was loaded to enable easier detection of the lower intensity fragment peaks. Samples were manually injected, and MS/MS fragmentation data were collected from m/z 50 up to 2000, depending on the initial m/z value and charge state of the precursor ion. Total run time was 55 min, applying a mass spectral scan rate of 1 spectra/sec. The delay time feature was used to bypass the void volume and fragmentation was only done during the relevant 2 min elution window. This 2 min window was begun 1 min before and ended 1 min after the targeted biomarker peak. Either argon (Q-Star) or nitrogen (Agilent) was used as the collision gas. Typically, 2-4 runs at different fixed collision energies were performed to obtain the broadest set of fragments for the peak of interest. Different spectra from different runs were first overlaid and then summed into a single composite MS2 spectrum using the Add Data feature in Analyst QS 1.1 instrument software.

Peptide Sequencing Via the Mascot Search Engine

The resultant MS2 fragmentation spectrum was evaluated manually and the peak m/z values and intensities were exported to an Excel sheet. Here, any incorrectly assigned charge states were corrected by comparing these peaks to the fragmentation data in the mass spectrum. To simplify the database search, all the peaks with charge state more than 1 in the adjusted data list were converted into their +1 m/z values using Formula I:

$$+1 \text{ mass} = \text{m/z value} * \text{charge} - (\text{charge} - 1\text{H}^+) \qquad \text{I}$$

This amended list of ions was pasted into a Mascot generic format file ('.mfg') and submitted to Mascot search engine. The '.mgf' file was uploaded and the parameters used for Mascot searches were: no enzyme digestion, Uni_human database, no modifications, peptide tolerance of 1.2 Da, and MS/MS tolerance of 0.6 Da. Protein Blast search was also used for peptides in an effort to identify the parent protein compound from which the peptide originated.

De Novo Sequencing of Peptides

On several occasions Mascot does not generate conclusive results. This is often due to incomplete b- or y-ion series. In such cases de novo sequencing was attempted, where the fragmentation spectrum was manually evaluated to assign amino acid identities by studying the mass differences between fragment ions. There are typically both b- and y-ions observed when collision-induced dissociation is performed. Interpretation can be complicated when both incomplete representation of b- and y-ions are seen. First, we attempt to identify the b1 and/or y1 ions to specify the starting point of the peptide sequence. Immonium ions found in the low m/z range (typically <200) often give indications about the amino acids present in the peptide sequence. Beginning with b1 or y1, mass differences between neighboring or near neighbor peaks in the MS2 spectra were studied. When a mass difference corresponded to the mass of an amino acid residue, this led to an assignment of identity to that amino acid, and then the next amino acid in the sequence was considered. The peak of the assigned amino acid was then used as a reference and the process was repeated to assign the next amino acid in the series starting from the b2- or y2-ion fragment peak. This continued until a sequence of all amino acids contained in a peptide was determined. For incomplete fragment coverage, the use of multiple collision energies and careful assignment often leads to a tentative sequence. This can be compared to known amino acid sequences using a BLAST search of all predicted and known proteins in the human using the NIH database. If the amino acid sequence is incorrect, no matches will be found. With small peptides, the amino acid sequence may not be unique to a single parent protein.

Lipid Identifications Employing Applied Biosystem's QSTAR Pulsar I Quadrupole Orthogonal Time-of-Flight Mass Spectrometer Fragmentation studies for lipids and their identification were carried out using the same instrument parameters as described in peptide identification studies above. The primary difference was that 1 or 2 collision energies were sufficient for fragmenting lipids. The peaks produced by fragmentation remained quite consistent across different collision energies but rather showed differences in intensities.

Lipid Fragmentation Experiments Employing Agilent 6530 Accurate-Mass Q-TOF LC/MS System Both instruments were used for fragmentation studies, each providing somewhat different information. For studies done with the Agilent instrument, the Dual ESI source was operated in positive ion mode and instrument parameters were set as follows: sheath gas temperature, 300° C.; sheath gas flow, 5 L/min; nebulizer, 15 psi; dry gas temperature, 300° C.; dry gas flow, 5 L/min; and capillary entrance voltage, 3500 V. Fragmentor and Skimmer1 were operated at 150 V and 65 V, respectively. The autosampler temperature was maintained at 4° C. The MS scan data were collected at a rate of 1 spectra/s over a range of m/z 110-2000. Data was acquired in both profile and centroid modes. A reference solution having ions at m/z 121.050873 and 922.009798 was used during these experiments to calibrate the MS. Reference nebulizer pressure was maintained at 5 psi while auto calibration reference parameters were detection window, 20 ppm and minimum height, 1000 counts. The reference standards allowed us to correct unknown masses and also allowed us to determine the day-to-day drift in mass accuracy to insure no instrument adjustment needed to be made. In the case of lipids, where exact mass matters more, this can be an important control. The software, MassHunter Data Acquisition B.06.00 (Agilent), MassHunter Qualitative Analysis B.05.01 (Agilent) permitted direct on-line data collection, extracting specific ion chromatograms and analysis.

Data-dependent Auto MS was most commonly used for fragmentation studies. However, if peak intensities were low, representing too few MS2 scans, then data independent targeted MS was also used. The MS and the MS/MS information were collected from m/z 50 and up. The ending m/z value depended on the mass of the parent lipid molecule insuring the range would include all the fragments of the parent lipid molecule. Typically, collision energies ranging from 15-30 were used for fragmentation. Not more than 3 different collision energies were used per run. Sometimes, a single collision energy was sufficient to obtain good fragmentation. Sometimes additional energies were needed. Isolation width of precursor ion was set as narrow (~1.3 m/z). A narrow width can markedly reduce the possibility of fragmenting neighboring peaks. Typically, MS scan rates and MS/MS scan rates were 1 spectra/sec although in a few cases scan rates of 2 spectra/sec were used. With a lower scan rate, more of the transients hit the detector, hence there was an increase in the gain, which helped in obtaining higher signal/noise ratio of the fragment ions. Data was collected in both centroid and profile modes.

Identification of Lipids

While fragmenting lipid biomarkers, a prominent peak at m/z 184.07 was frequently observed. This is indicative of a phosphatidylcholine head group, a distinctive feature. With lipids there were not as many fragments produced as typically seen in peptide fragmentation spectra. Increasing the collision energies did not result in more fragmentation, but primarily resulted in an alteration of peak intensities for the fragments that were already seen.

To further characterize lipid biomarkers, a search was performed on Lipidmaps, the primary database of known lipids using the mass of the neutral precursor ion ((M+H+)–H+). Fragmentation data are not available, and fragmentation spectra cannot be compared with archived fragmentation patterns. Consequently, the database provided a selection of elemental compositions having similar masses to the experimentally observed parent mass, from very similar m/z values to others that were more unlikely. Those closest in m/z to the molecule of interest were specifically focused on. Second, only those classes of lipids that contained the phosphatidylcholine, as seen for the AD biomarkers described here, were considered. Fragments were also found indicative of a glycerophosphatidylcholine. This indicated the general category of lipid. These measures limited the pool of candidates dramatically. Then a more careful analysis of the MS2 fragments was conducted, looking for fragments representing the 2 fatty acids that modified the glycerol backbone. This was often successful, but did not allow assignment of fatty acids to the sn1 or sn2 positions on the glycerol. In cases of lipid oxidation, chemically unsaturated fatty acids would be those predominantly modified, however in the MS2 fragmentation, the oxygen containing fatty acid may or may not remain intact. The nature of the oxygen containing species could in many cases be decided based on fragmentation, however, even in the most highly characterized studies, an unequivocal location of the oxidation site and the exact nature of the oxidation species, can often not be determined by MS and other instrumental approaches or chemical tests are not available given the very, very low concentrations of the relevant biomarkers.

Using MS-MS approaches, the class and elemental composition of a lipid can be determined, and the length and double bond character of fatty acids can be provided without knowing the location of the double bonds. In glycerophospholipids, the location of the fatty acids on the glycerol backbone cannot be determined as to which fatty acid is attached to sn1 and which to sn2. Oxidation of lipids can be determined including the general nature of the oxygen containing side group. Again, while oxidations will occur predominantly at double bonds, if there are more than one double bond present, which double bond(s) is involved cannot be conclusively determined by MS.

Given the very, low abundance of these biomarkers, no other instrumental method, e.g. NMR, is possible. Using lipids of known composition and causing their oxidation, then submitting them to MS and MS2 analysis would also not provide additional structural information. Furthermore, standards of possible compounds are not typically available. Previously published research was considered in predicting bond breakage and the consequent fragments produced from glycerophosphatidylcholine molecules, but the few published reports that provide MS2 data do not elucidate double bond placement or differentiation of sn1 or sn2 fatty acid location.

Some biomarkers were oxidized lipid molecules and certain fragments indicative of loss of oxygen were observed. In case of hydroxylated species, fragment ions have odd number m/z value and show fragments representing neutral water loss (−18 mass units). For a neutral loss of 32 mass units, the likely explanation is the loss of —OOH. These oxidized lipids represent the effects of reactive oxygen species generated by oxidative stress processes in the human. Oxidized lipid molecules are not found in the Lipidmaps database.

Statistical Analysis Including Construction of Multi-Marker Model Using Validated Biomarkers The Student's t-test was used to evaluate the performance of the 13 candidate markers retested in the replication study. A p-value <0.05 was considered significant. The biomarker also had to show the same trend comparing cases to controls. We further studied different combinations of the statistically significant candidate biomarkers to find out if panels of markers provided better diagnostic discrimination. Given the small number of candidate biomarkers, logistic regression analysis was used to consider combinations providing a receiver operator characteristic curve (a plot of sensitivity, i.e. true positive, versus 1-specificity, i.e. true negative) from which could be calculated an area under the curve (AUC) and a sensitivity at any given specificity.

Results—Biomarker Study II

Validation of Previously Found Biomarkers that Showed Significant Diagnostic Discrimination One focus of this study was to determine how well the 13 biomarkers that had performed most consistently in the Biomarker Study I would perform in the validation study. Of these 13, the biomarkers m/z 708.3 and 660.4 were not clearly seen in most of the current samples. In the case of m/z 708.3, in the validation set, there was a large, unrelated peak that likely led to variable ion suppression. Moreover, there was also in these specimens an overlapping peptide envelope, which made calculation unreliable. For the peak m/z 660.4 the intensity was too low to determine peak height or area with confidence. Hence, these two could not be analyzed at this time.

The extracted MS data obtained for the remaining biomarkers was sent to the independent arbiter who conducted the analyses and maintained the blind. The data was tested in two ways: 1) non-demented, matched controls (CDR=0) vs. any stage AD cases, i.e. a CDR of 0.5 or greater) or 2) matched, non-demented controls (CDR=0) vs. the earliest stage AD only (CDR=0.5). Among the remaining 11 biomarkers, m/z 602.3, 804.55 and 874.6 were significantly different between cases and controls for all 4 comparisons and followed the same trend as observed in Biomarker Study I.

Similar to the data from Biomarker Study I, it was discovered that there were 2 candidate biomarkers with the same nominal m/z of 804.5, but offset somewhat in elution time from the 804.55 that validated. To insure that there was no misinterpretation of the data, both species were included. The second species had an m/z of 804.53 but eluted later between 39.5-41.5 min (the 804.55 eluted between 33-35 min). This species had been a significant biomarker in the initial data but was not part of the subset of 13. The candidate at m/z 804.53 in the later hydrophobic region also passed the validation. Cases had significantly higher quantities compared with controls in the validation set just as in the preliminary study. Table 4 shows results for of the validation of these biomarkers. Among the validated biomarkers, all were higher in the cases. This applied for comparisons between different stages of AD for these biomarkers as well.

TABLE 4

Student's t-test results

| Biomarker m/z | Charge | Retention Time (mm) | CDR 0 vs CDR > 0 p-value | CDR 0 vs CDR 0.5 p-value |
|---|---|---|---|---|
| 602.3 | 1 | 19.5-22.5 | 0.0014 | $8.41 \times 10^{-5}$ |
| 804.55 | 1 | 33-35 | $3.60 \times 10^{-7}$ | $1.75 \times 10^{-8}$ |
| 874.59 | 1 | 40-44 | $6.37 \times 10^{-5}$ | $3.00 \times 10^{-5}$ |
| 804.53 | 1 | 39.5-41.5 | $9.48 \times 10^{-7}$ | $1.37 \times 10^{-6}$ |

Table 4 provides the Student's t-test results showing p values obtained for the unnormalized validation data. Different stages are compared and p values for them are listed in the table as well. Trends indicating whether values were higher in cases or controls were also studied. Observation was made if they followed the same or opposite trend. In the last column it is indicated of the biomarker passed the validation study.

Identification of the Validated Biomarkers

The 4 biomarkers that validated in the replication set were analyzed for chemical identification. MS2 data demonstrated that 1 of these biomarkers was a peptide and 3 were glycerophosphocholine lipids. The structural features that can be obtained from MS studies are summarized for each of the 4 biomarkers as follows:

1. Biomarker 602.3 (charge state 1) is a peptide with sequence of amino acids L/IAENR (SEQ ID NO: 001), data for which is shown in Table 5.

TABLE 5

| Amino acids | Calculated b ions | Calculated y ions | Observed b ions | Observed y ions | Immonium ions |
|---|---|---|---|---|---|
| L/I | 114.0919 | 602.3262 | Absent | 602.3079 | 86.078 |
| A | 185.1291 | 489.2422 | 185.1247 | 489.1749 | |
| E | 314.1716 | 418.2051 | 314.1593 | 418.1749 | |
| N | 428.2146 | 289.1625 | 428.2129 | 289.1574 | |
| R | 584.3157 | 175.1196 | 584.2684 | 175.1022 | |

2. Biomarker 804.55 (charge state 1, 33-35 min) is a glycerophosphatidylcholine with two fatty acid acyl side chains, one having 18 carbon atoms and 2 double bonds (18:2), and the other having 20 carbon atoms and 5 double bonds (20:5, very likely to be eicosapentaenoic acid). The positions of the double bonds can be difficult to determine with certainty. A fragment seen at m/z 542.3153 confirms the presence of a fatty acid (18:2) and a fragment observed at m/z 520.3815 confirms the presence of a second fatty acid (20:5). The molecular formula for its neutral and protonated states are as follows: $[C_{46}H_{78}NO_8P]+H^+$.

3. Biomarker 874.59 (charge state 1) is an oxidized glycerophosphatidylcholine. The molecular formula for the neutral and protonated species are $[C_{46}H_{84}NO_{12}P]+H^+$. The fatty acid side chains have 38 carbons total and 4 double bonds total. A peak in the MS2 is consistent with the presence of palmitic acid (C16:0). This indicates that the other fatty acid has 22 carbons and 4 double bonds. The second fatty acid has been oxidized, most likely as follows [22:4+(—OOH)$_2$]+H$^+$. Fragments show the loss of —OOH but not the loss of O or H$_2$O (as would occur with a —OH group). This species, or a very similar species, has been described in the literature as an oxidation product (Ingram, Homer et al. 2003).

4. Biomarker 804.53 (charge state 1) eluting at retention time 39.5-41.5 min is an oxidized glycerophosphatidylcholine having a neutral and protonated elemental composition of [C$_{42}$H$_{78}$NO$_{11}$P+H$^+$]. The glycerol molecule is modified by two fatty acids with total carbon number of 34 with 2 double bonds. One of the fatty acids is palmitic acid (C16:0) based on its fragment being present in the MS2 spectra. The other fatty acid is C18:2, and is the oxidized species. It likely contain one —OOH and one keto group. The second fatty acid, containing double bonds, has been oxidized and the same or similar oxidized lipid has been described (Pereira 2006).

Constructing Multi-Marker Diagnostic Panels for AD

Figure 1A:
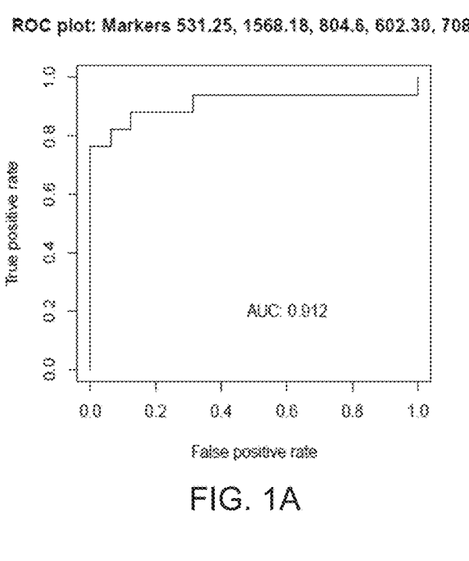
FIG. 1A is a Receiver Operating Characteristic (ROC) plot for various markers in accordance with one aspect of the present disclosure.
Figure 1B:
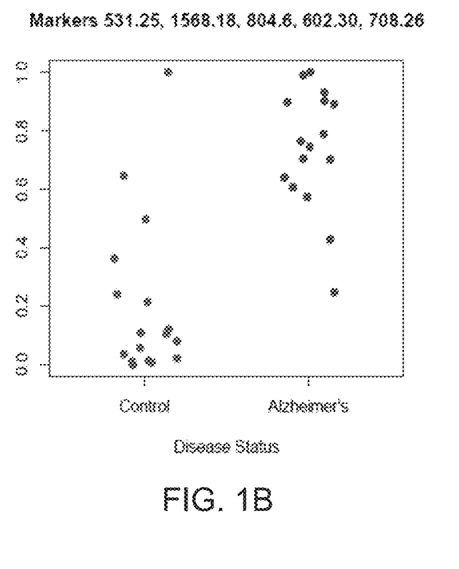
FIG. 1B is a plot of predicted probability vs. disease state for the various markers evaluated in FIG. 1A in accordance with another aspect of the present disclosure.
Figure 2A:
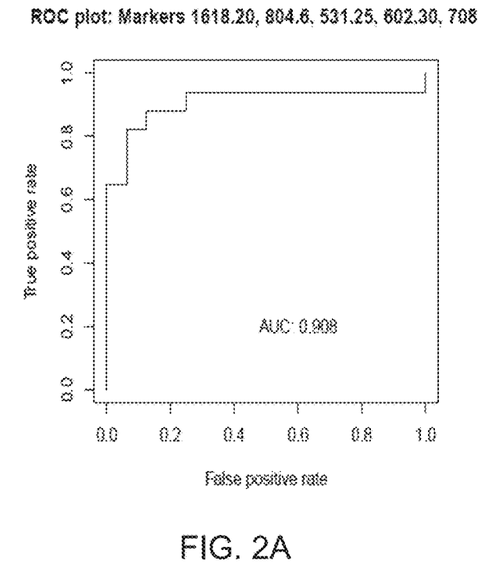
FIG. 2A is a ROC plot for various markers in accordance with another aspect of the present disclosure.
Figure 2B:
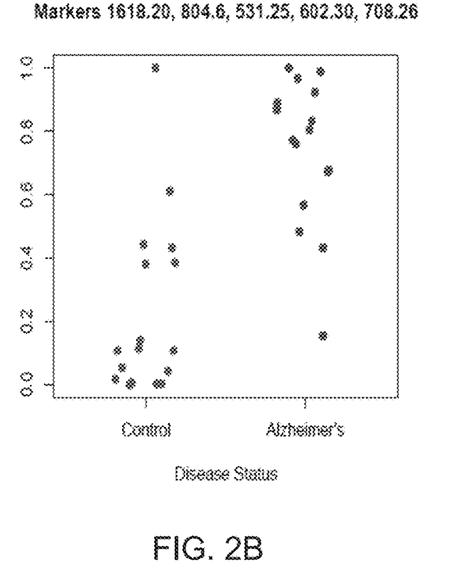
FIG. 2B is a plot of predicted probability vs. disease state for the various markers evaluated in FIG. 2A in accordance with another aspect of the present disclosure.
Figure 3:
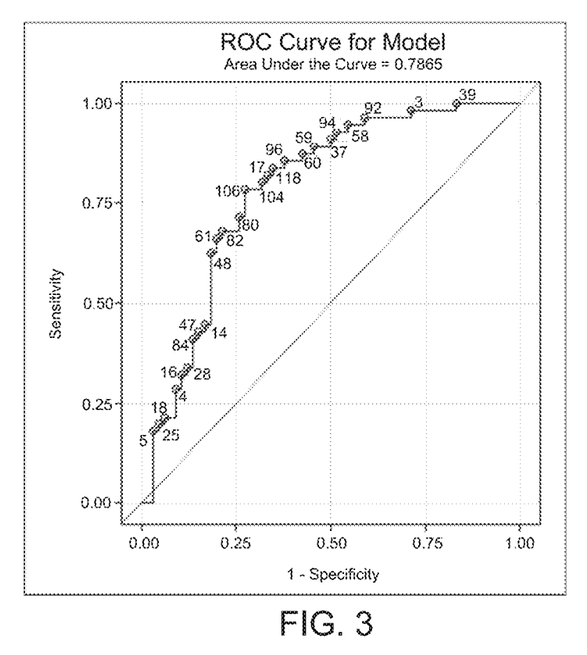
FIG. 3 is a ROC plot for various markers in accordance with another aspect of the present disclosure.
Figure 4:
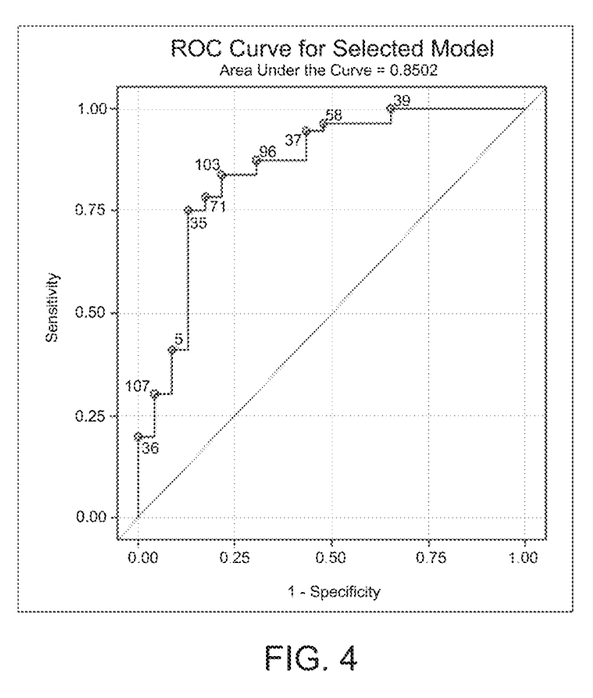
FIG. 4 is a ROC plot for various markers in accordance with another aspect of the present disclosure.

Logistic regression analysis was performed to evaluate the ability of multi-marker models to diagnose AD. They were attempted for any stage AD as well for the very earliest stage of AD (CDR=0.5). This same statistical approach was also used in Biomarker Study I, but was supplemented with other statistical comparisons. In this approach, all possible combinations of the 4 biomarkers were considered. The analysis provides a receiver operator characteristic plot of the performance of the model in correctly identifying cases (sensitivity) as a function of the false positive rate (1-true negative rate/specificity). When comparing controls (CDR=0) vs. any stage AD cases (CDR=0.5, 1, 2), one good model was obtained by using all four validated biomarkers (602.3, 804.6, 874.6, 804.5) as is shown in FIG. 3, having an AUC=0.7865. This provides a sensitivity of ~70% for a specificity of ~80%. The curve represents biomarkers that were statistically different between non-demented controls (CDR=0) vs. any stage AD (CDR=0.5, 1.0, 2.0). When comparing controls (CDR=0) vs. early stage AD (CDR=0.5), one good multi-marker panel is the combination of biomarker m/z 804.6 and biomarker 602.3, as is shown in FIG. 4, with an AUC=0.8502. This provides a sensitivity of ~85% for a specificity of ~80%. The curve represents biomarkers that were statistically different between non-demented controls (CDR=0) vs. mild stage AD (CDR=0.5). As such, this approach provides useful biomarkers and biomarker combinations that correctly diagnose the greater majority of individuals with AD, even the earliest stage of AD.

Of course, it is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been described above with particularity and detail in connection with what is presently deemed to be the most practical embodiments of the disclosure, it will be apparent to those of ordinary skill in the art that numerous modifications, including, but not limited to, variations in size, materials, shape, form, function and manner of operation, assembly and use may be made without departing from the principles and concepts set forth herein.

The invention claimed is:

1. A method comprising:
assaying a biological medium to determine the presence of a biomarker selected from the group consisting of Biomarker 1, Biomarker 2, Biomarker 3, Biomarker 4, and combinations thereof;
wherein Biomarker 1 is a peptide having an amino acid sequence L/IAENR (SEQ ID NO: 001) and has a mass-to-charge ratio (m/z) of 602.3 at a charge state of 1, Biomarker 2 has a molecular formula of [C$_{46}$H$_{78}$NO$_8$P]$^+$H$^+$ and has a m/z of 804.6 at a charge state of 1, Biomarker 3 has a molecular formula of [C$_{46}$H$_{84}$NO$_{12}$P]$^+$H$^+$ and has a m/z of 874.6 at a charge state of 1, and Biomarker 4 has a molecular formula of [C$_{42}$H$_{78}$NO$_{11}$P$^+$H$^+$] and has a m/z of 804.5 at a charge state of 1, and wherein the presence of the biomarkers in the individual indicates the presence of Alzheimer's disease; and
administering a treatment for Alzheimer's disease to the individual.

2. The method of claim 1, wherein the biological medium is assayed for two or more biomarkers selected from the group consisting of Biomarker 1, Biomarker 2, Biomarker 3, and Biomarker 4.

3. The method of claim 1, wherein the biological medium is assayed for three or more biomarkers selected from the group consisting of Biomarker 1, Biomarker 2, Biomarker 3, and Biomarker 4.

4. The method of claim 1, wherein the biological medium is assayed for Biomarker 1, Biomarker 2, Biomarker 3, and Biomarker 4.

5. The method of claim 1, wherein the biological medium is assayed for Biomarker 1 and Biomarker 2.

6. The method of claim 1, wherein the biological medium is a biological fluid.

7. The method of claim 6, wherein the biological fluid is serum.

8. The method of claim 1, wherein assaying the biological medium further includes assaying the biological medium using mass spectrometry for the biomarker.

9. The method of claim 8, wherein the mass spectrometry is tandem mass spectrometry.

\* \* \* \* \*

```
                        SEQUENCE LISTING

<160> NUMBER OF SEQ ID NOS: 1

<210> SEQ ID NO 1
<211> LENGTH: 5
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Leu (L) or Ile (I)

<400> SEQUENCE: 1

Xaa Ala Glu Asn Arg
1               5
```